United States Patent
Matsumoto et al.

(10) Patent No.: US 11,714,988 B2
(45) Date of Patent: Aug. 1, 2023

(54) WIRELESS IC TAG-ATTACHED METAL MEDICAL INSTRUMENT

(71) Applicant: Murata Manufacturing Co., Ltd., Nagaokakyo (JP)

(72) Inventors: Kengo Matsumoto, Nagaokakyo (JP); Hiromi Murayama, Nagaokakyo (JP); Makoto Yasutake, Nagaokakyo (JP); Tsuyoshi Suesada, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 58 days.

(21) Appl. No.: 17/550,709

(22) Filed: Dec. 14, 2021

(65) Prior Publication Data
US 2022/0108144 A1    Apr. 7, 2022

Related U.S. Application Data (63) Continuation of application No. PCT/JP2020/032274, filed on Aug. 27, 2020.

(30) Foreign Application Priority Data

Sep. 5, 2019   (JP) ................. 2019-161892

(51) Int. Cl.
G06K 19/077 (2006.01)
H01F 27/06 (2006.01)

(52) U.S. Cl.
CPC ........ G06K 19/07758 (2013.01); H01F 27/06 (2013.01)

(58) Field of Classification Search
CPC ............................................. G06K 19/07758
(Continued)

(56) References Cited

U.S. PATENT DOCUMENTS 11,596,291 B2   3/2023   Harris et al.
2006/0145871 A1 * 7/2006 Donati ............... A61B 90/98
                                                 340/539.1
(Continued)

FOREIGN PATENT DOCUMENTS

CN   112955990 A   6/2021
JP   4069958 B2   4/2008
(Continued)

OTHER PUBLICATIONS

International Search Report issued for PCT/JP2020/032273, dated Nov. 2, 2020.
(Continued)

*Primary Examiner* — Allyson N Trail
(74) *Attorney, Agent, or Firm* — ArentFox Schiff LLP (57) ABSTRACT

A wireless IC tag-attached metal medical instrument includes a metal medical instrument including a metal portion. The metal medical instrument is configured such that electric, magnetic, or electromagnetic field coupling is established between a resonant circuit and the metal portion when a wireless IC tag is fixed to the metal portion that includes the resonant circuit having an inductor with a spiral or helix shape that turns around a central axis more than one turn. In this configuration, the metal portion either emits a transmission signal with a frequency equal to a resonant frequency of an electromagnetic wave supplied from the resonant circuit or receives a reception signal having a frequency equal to the resonant frequency, and supplies the reception signal to the resonant circuit.

20 Claims, 6 Drawing Sheets

(58) Field of Classification Search
USPC .......................................................... 235/492
See application file for complete search history.

(56) References Cited

U.S. PATENT DOCUMENTS

| | | | |
|---|---|---|---|
| 2008/0238631 A1 | 10/2008 | Blake et al. | |
| 2010/0289626 A1 | 11/2010 | Oberle et al. | |
| 2017/0258551 A1* | 9/2017 | Smith .................... | G16H 40/20 |
| 2020/0031067 A1 | 1/2020 | Itakura et al. | |
| 2020/0160005 A1* | 5/2020 | Volpi .................... | G06Q 10/087 |
| 2021/0077111 A1 | 3/2021 | Adams et al. | |
| 2022/0096202 A1 | 3/2022 | Murayama et al. | |
| 2022/0104918 A1* | 4/2022 | Matsumoto .............. | H01Q 1/44 |
| 2022/0108144 A1 | 4/2022 | Matsumoto et al. | |
| 2022/0287797 A1 | 9/2022 | Hoegerle et al. | |
| 2022/0328170 A1 | 10/2022 | Bilsøe | |
| 2022/0395340 A1 | 12/2022 | Dumpe | |
| 2022/0395344 A1 | 12/2022 | Wham et al. | |

FOREIGN PATENT DOCUMENTS

| | | | |
|---|---|---|---|
| JP | 2019185494 A | 10/2019 |
| WO | 2018181526 A1 | 10/2018 |
| WO | 2019004439 A1 | 1/2019 |

OTHER PUBLICATIONS

International Search Report issued for PCT/JP2020/032275, dated Nov. 2, 2020.
International Search Report issued for PCT/JP2020/032274, dated Nov. 2, 2020.
Written Opinion of the International Searching Authority issued for PCT/JP2020/032274, dated Nov. 2, 2020.

\* cited by examiner

WIRELESS IC TAG-ATTACHED METAL MEDICAL INSTRUMENT

CROSS REFERENCE TO RELATED APPLICATIONS

The present application is a continuation of PCT/JP2020/032274 filed Aug. 27, 2020, which claims priority to Japanese Patent Application No. 2019-161892, filed Sep. 5, 2019, the entire contents of each of which are incorporated herein by reference.

TECHNICAL FIELD

The present invention relates to a wireless IC tag-attached metal medical instrument including a wireless IC tag and a metal medical instrument.

BACKGROUND

Conventional wireless IC tags are known, for example, as described in Japanese Patent No. 4069958 (hereinafter "Patent Literature 1"). The wireless IC device disclosed therein includes a wireless IC chip, a resonant circuit, and an antenna. The resonant circuit is connected to the wireless IC chip. The resonant circuit has a predetermined resonant frequency. Moreover, the antenna transmits a transmission signal supplied from the resonant circuit and/or receives a reception signal and supplies the reception signal to the resonant circuit. In the field of such wireless IC devices, various devices have been proposed in order to increase the communication distance.

Moreover, it has been proposed to use the wireless IC device described in Patent Literature 1 in the field of metal medical instruments. Specifically, it has been proposed that a wireless IC tag is attached to a metal medical instrument to be used as a wireless IC device. In this case, the metal medical instrument functions as an antenna. As a result, management of the metal medical instrument becomes easy.

In general, there are many types of metal medical instruments. In addition, many types of metal medical instruments are used under many types of use environments. Accordingly, it is required to attach a wireless IC tag to a metal medical instrument by an attachment method suitable for a use environment of the metal medical instrument.

SUMMARY OF THE INVENTION

Therefore, it is an object of the present invention to provide a wireless IC tag-attached metal medical instrument constructed to improve the degree of freedom in a method for attaching a wireless IC tag.

As a result of a study by the inventor to improve the degree of freedom in a method for attaching a wireless IC tag to a metal medical instrument, it has been appreciated that a resonant frequency of a resonant circuit of the wireless IC tag varies when the method for attaching the wireless IC tag changes. For example, there is a case where the wireless IC tag is attached to the metal medical instrument by welding. In this case, a mounting bracket is used. Thus, a capacitance is generated between the mounting bracket and the resonant circuit, or the mounting bracket obstructs a magnetic flux, so that the resonant frequency of the resonant circuit varies. In addition, there is a case where the wireless IC tag is covered with a resin. In this case, the permittivity around the wireless IC tag varies so that the resonant frequency of the resonant circuit varies. When the resonant frequency of the resonant circuit varies in this manner, it is preferable that a communication band of a wireless IC tag-attached metal medical instrument be wide. As a result, the wireless IC tag-attached metal medical instrument can transmit and receive a high-frequency signal having a frequency slightly deviated from the resonant frequency of the resonant circuit.

However, there is a trade-off relationship between widening the communication band of the wireless IC tag-attached metal medical instrument and increasing the communication distance of the wireless IC tag-attached metal medical instrument. Specifically, it is preferable to decrease a Q-factor of the resonant circuit in order to widen the communication band of the wireless IC tag-attached metal medical instrument. However, when the Q-factor of the resonant circuit decreases, the communication distance of the wireless IC tag-attached metal medical instrument also decreases. As described above, it is a major issue to increase the communication distance of the wireless IC tag-attached metal medical instrument in the field of wireless IC devices. Thus, those skilled in the art hesitate to decrease the Q-factor of the resonant circuit even if the communication band of the wireless IC tag-attached metal medical instrument is widened.

Therefore, the inventor of the present application has studied a use situation of wireless IC tag-attached metal medical instruments. The wireless IC tag-attached metal medical instruments are disposed side by side on a tray, for example. Then, the operator positions a reader/writer on the tray to cause the reader/writer and the wireless IC tag-attached metal medical instrument to communicate with each other. In this configuration, the inventor determined that the distance between the reader/writer and the wireless IC tag-attached metal medical instrument is relatively short. Therefore, the present application conceives that widening the communication band of the wireless IC tag-attached metal medical instrument can be prioritized over increasing the communication distance of the wireless IC tag-attached metal medical instrument.

In order to solve the above-described problem, the exemplary embodiment of the present invention adopts the following configuration.

According to an exemplary aspect, a wireless IC tag-attached metal medical instrument (1) is provided that includes a wireless IC tag that includes a resonant circuit including an inductor, and a wireless IC chip. Moreover, the resonant circuit is electrically connected to the wireless IC chip and has a predetermined resonant frequency, the inductor has a spiral shape or a helix shape that turns around a central axis more than one turn; and a metal medical instrument includes a metal portion. The metal medical instrument is configured such that electric field coupling, magnetic field coupling, or electromagnetic field coupling is established between the resonant circuit and the metal portion of the metal medical instrument, and the metal portion of the metal medical instrument is configured to perform either of (A) and/or (B) when the wireless IC tag including the resonant circuit is fixed to the metal portion of the metal medical instrument. Specifically, for function (A), the metal portion of the metal medical instrument emits a transmission signal, which has a frequency equal to the predetermined resonant frequency and is supplied from the resonant circuit, as an electromagnetic wave. Moreover, for function (B), the metal portion of the metal medical instrument receives a reception signal having a frequency equal to the predetermined resonant frequency as an electromagnetic wave, and supplies the reception signal to the resonant circuit.

According to the wireless IC tag-attached metal medical instrument (1), the degree of freedom in a method for attaching the wireless IC tag is improved. More specifically, in the wireless IC tag-attached metal medical instrument (1), the wireless IC tag including the resonant circuit, which includes the inductor having the spiral shape or helix shape that turns around the central axis more than one turn, is fixed to the metal portion of the metal medical instrument, so that the electric field coupling, magnetic field coupling, or electromagnetic field coupling is established between the resonant circuit and the metal portion of the metal medical instrument. That is, an inductance value of the inductor is large in the wireless IC tag-attached metal medical instrument (1). As the inductance value of the inductor increases, a Q-factor of the resonant circuit decreases. Therefore, a communication band of the wireless IC tag-attached metal medical instrument (1) is widened. As a result, the wireless IC tag-attached metal medical instrument (1) is configured to transmit and receive a high-frequency signal having a frequency slightly deviated from the resonant frequency of the resonant circuit. Even when the resonant frequency of the resonant circuit of the wireless IC tag varies due to a change in the method for attaching the wireless IC tag, the wireless IC tag-attached metal medical instrument (1) can transmit the high-frequency signal and/or receive the high frequency signal. As described above, the degree of freedom in the method for attaching the wireless IC tag is improved according to the wireless IC tag-attached metal medical instrument (1).

Moreover, a wireless IC tag-attached metal medical instrument (2) is the wireless IC tag-attached metal medical instrument (1) in which the metal medical instrument is a general medical device belonging to Class I in the Japanese Medical Device Nomenclature.

It is recommended to attach the wireless IC tag to a general medical device belonging to Class I in the Japanese medical device name. Therefore, in the wireless IC tag-attached metal medical instrument (2), the metal medical instrument is the general medical device belonging to Class I in the Japanese Medical Device Nomenclature.

A wireless IC tag-attached metal medical instrument (3) is the wireless IC tag-attached metal medical instrument (1) or (2) in which the metal medical instrument is a small steel article.

It is recommended to attach the wireless IC tag to a small steel article. Therefore, in the wireless IC tag-attached metal medical instrument (3), the metal medical instrument is the small steel article.

A wireless IC tag-attached metal medical instrument (4) is the wireless IC tag-attached metal medical instrument (1) to (3). The wireless IC tag-attached metal medical instrument further includes a resin portion that covers the wireless IC tag such that the wireless IC tag is not exposed.

In the wireless IC tag-attached metal medical instrument (4), the wireless IC tag is covered with the resin portion. Thus, the wireless IC tag is protected by the resin portion.

A wireless IC tag-attached metal medical instrument (5) is the wireless IC tag-attached metal medical instrument (1) to (4) in which the inductor has a spiral shape or a helix shape that turns around the central axis two or more turns.

According to the wireless IC tag-attached metal medical instrument (5), the inductance value of the inductor is further increased. As a result, the Q-factor of the resonant circuit decreases, and the communication band of the wireless IC tag-attached metal medical instrument (5) is widened.

A wireless IC tag-attached metal medical instrument (6) is the wireless IC tag-attached metal medical instrument (1) to (5) in which the wireless IC tag is fixed to the metal portion of the metal medical instrument with a resin adhesive.

According to the wireless IC tag-attached metal medical instrument (6), the wireless IC tag is fixed to the metal portion of the metal medical instrument with the resin adhesive, and thus, a fixing member or the like for fixing the wireless IC tag to the metal portion is unnecessary. Thus, it is easy to fix the wireless IC tag to the metal portion.

A wireless IC tag-attached metal medical instrument (7) is the wireless IC tag-attached metal medical instrument (1) to (5) in which the wireless IC tag is fixed to the metal portion of the metal medical instrument by welding.

According to the wireless IC tag-attached metal medical instrument (7), the wireless IC tag is fixed to the metal portion of the metal medical instrument by welding, and thus, detachment of the wireless IC tag from the metal portion due to an environmental change, such as a temperature change, is reduced.

A wireless IC tag-attached metal medical instrument (8) is the wireless IC tag-attached metal medical instrument (1) to (7) in which the predetermined resonant frequency belongs to an ultrahigh frequency (UHF) frequency band.

A wireless IC tag-attached metal medical instrument (9) is the wireless IC tag-attached metal medical instrument (1) to (8). The wireless IC tag-attached metal medical instrument communicates with a reader/writer via an electromagnetic wave.

The above-described object and other objects, features, aspects, and advantages of the present invention will become more apparent from the following detailed description of an exemplary embodiment of the present invention given with reference to the accompanying drawings.

It is noted that as used in the present specification, the term "and/or" includes any and all combinations of one or a plurality of the associated listed items.

Moreover, as used the present this specification, the terms "including", "comprising" or "having" and variations thereof specify the presence of stated features, steps, operations, elements, components, and/or their equivalents, but may also include one or a plurality of steps, operations, elements, components, and/or groups thereof.

Unless otherwise defined, all terms (including technical and scientific terms) used in the present specification have the same meaning as commonly understood by those skilled in the art to which the present teaching belongs.

In the description of the exemplary embodiment, it will be understood that the number of techniques and the number of steps are disclosed. Each of these has individual benefit, and each can also be used in conjunction with one or more, or in some cases all, of the other disclosed techniques. Therefore, this description refrains from repeating every possible combination of the individual steps in an unnecessary fashion for the sake of clarity.

In the following description, for purposes of explanation, numerous specific details are set forth in order to provide a thorough understanding of the exemplary embodiment of the present invention. However, it will be apparent to those skilled in the art that the present invention can be practiced without these specific details. The present disclosure is to be considered as an illustration of the present invention, and is not intended to limit the present invention to the specific embodiments illustrated by the following drawings or description.

According to the present invention, the degree of freedom in the method for attaching the wireless IC tag can be improved.

DETAILED DESCRIPTION OF EMBODIMENTS

Exemplary Embodiment

[Configuration of Wireless IC Tag-Attached Metal Medical Instrument]

Figure 1:
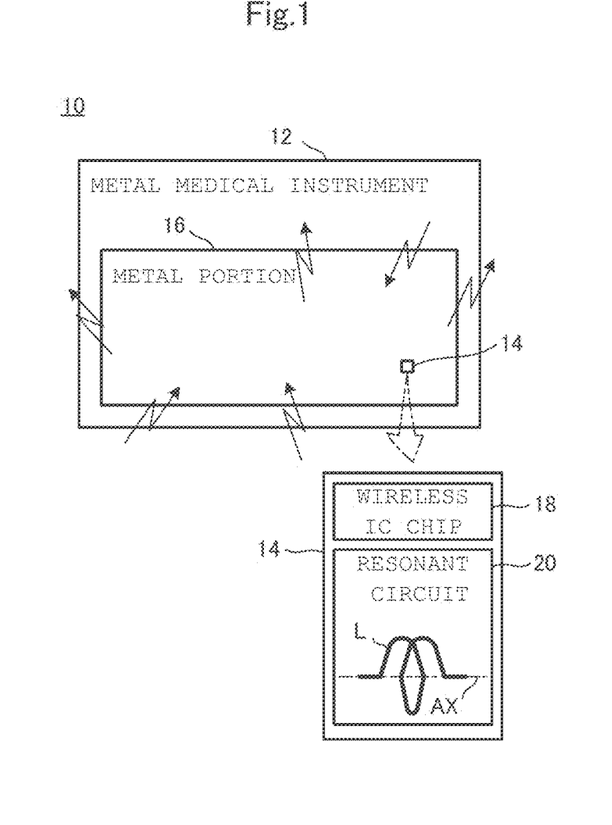
FIG. 1 is a configuration diagram of a wireless IC tag-attached metal medical instrument 10 according to an exemplary embodiment.

Hereinafter, a wireless IC tag-attached metal medical instrument 10 according to an exemplary embodiment will be described with reference to FIG. 1. FIG. 1 is a configuration diagram of the wireless IC tag-attached metal medical instrument 10 according to the embodiment of the present invention. FIG. 1 illustrates a block diagram of the wireless IC tag-attached metal medical instrument 10 and a block diagram of a wireless IC tag 14.

In the present specification, it is noted that an axis or a member extending in a front-back direction does not necessarily indicate only the axis or member parallel to the front-back direction. The axis or member extending in the front-back direction is the axis or member inclined within a range of ±45° with respect to the front-back direction. Similarly, an axis or a member extending in an up-down direction is the axis or member inclined within a range of ±45° with respect to the up-down direction. An axis or a member extending in a left-right direction is the axis or member inclined within a range of ±45° with respect to the left-right direction.

In the present specification, a case where a first member is supported by a second member includes a case where the first member is attached to the second member so as to be immovable with respect to the second member (i.e., fixed) and a case where the first member is attached to the second member so as to be movable with respect to the second member. The case where the first member is supported by the second member further includes both of a case where the first member is directly attached to the second member and a case where the first member is attached to the second member with a third member interposed therebetween. It is also noted that the first member, the second member, and the third member are included in the wireless IC tag-attached metal medical instrument 10.

In the present specification, the first member and the second member arrayed in the front-back direction indicate the following state. Both the first member and the second member are in the state of being disposed on an arbitrary straight line indicating the front-back direction when the first member and the second member are viewed in a direction perpendicular to the front-back direction. In the present specification, the first member and the second member arrayed in the front-back direction when viewed in the up-down direction indicate the following state. Both the first member and the second member are disposed on an arbitrary straight line indicating the front-back direction when the first member and the second member are viewed in the up-down direction. In this case, anyone of the first member and the second member is not necessarily disposed on an arbitrary straight line indicating the front-back direction when the first member and the second member are viewed from the left-right direction different from the up-down direction. Note that the first member and the second member may be in contact with each other. The first member and the second member may be separated from each other. The third member may be present between the first member and the second member. It should be appreciated that this definition also applies to directions other than the front-back direction.

In the present specification, the first member disposed in front of the second member indicates the following state. At least a part of the first member is disposed in a region through which the second member passes at the time of moving in parallel in the forward direction. Accordingly, the first member may be accommodated in the region through which the second member passes at the time of moving in parallel in the forward direction, or may protrude from the region through which the second member passes at the time of moving in parallel in the forward direction. In this case, the first member and the second member are arrayed in the front-back direction. This definition also applies to directions other than the front-back direction.

In the present specification, the first member being disposed in front of the second member when viewed in the left-right direction indicates the following state. The first member and the second member are arrayed in the front-back direction when viewed in the left-right direction, and a portion of the first member facing the second member is disposed in front of the second member when viewed in the left-right direction. In this definition, the first member and the second member are not necessarily arrayed in the front-back direction in three dimensions. This definition also applies to directions other than the front-back direction.

In the present specification, the first member disposed more frontward than the second member indicates the following state.

The first member is disposed in front of a plane which passes through a front end of the second member and is orthogonal to the front-back direction. In this case, the first member and the second member may be arrayed or are not necessarily arrayed in the front-back direction. It should be appreciated that this definition also applies to directions other than the front-back direction.

In the present specification, each portion of the first member is defined as follows unless otherwise specified. A front portion of the first member means the front half of the first member. A back portion of the first member means the back half of the first member. A left portion of the first member means the left half of the first member. A right portion of the first member means the right half of the first member. An upper portion of the first member means the upper half of the first member. A lower portion of the first member means the lower half of the first member. A front end of the first member means an end of the first member in the forward direction. A back end of the first member means an end of the first member in the backward direction. A left end of the first member means an end of the first member in the leftward direction. A right end of the first member means an end of the first member in the rightward direction. An upper end of the first member means an end of the first member in the upward direction. The lower end of the first member means an end of the first member in the downward direction. A front end portion of the first member means the front end of the first member and the vicinity thereof. A back end portion of the first member means the back end of the first member and the vicinity thereof. A left end portion of the first member means the left end of the first member and the vicinity thereof. A right end portion of the first member means the right end of the first member and the vicinity thereof. An upper end portion of the first member means the upper end of the first member and the vicinity thereof. A lower end portion of the first member means the lower end of the first member and the vicinity thereof.

The wireless IC tag-attached metal medical instrument 10 includes a metal medical instrument 12 and the wireless IC tag 14. It is noted that the wireless IC tag-attached metal medical instrument 10 may further include a configuration other than the metal medical instrument 12 and the wireless IC tag 14.

The wireless IC tag 14 includes a wireless IC chip 18 and a resonant circuit 20. Note that the wireless IC tag 14 may further include a configuration other than the wireless IC chip 18 and the resonant circuit 20.

In the exemplary aspect, the resonant circuit 20 is electrically connected to the wireless IC chip 18. Moreover, the resonant circuit 20 includes an inductor L that has a spiral shape or a helix shape that turns around a central axis Ax more than one turn. The spiral shape is a shape that turns around the central axis Ax on a plane. Therefore, the spiral shape is a two-dimensional shape. The helix shape is a shape that turns around the central axis Ax while traveling along the central axis Ax. Therefore, the helix shape is a three-dimensional shape. The spiral shape and the helix shape may have a continuously deformed shape having no corner, or may have an angular shape in an alternative aspect. When the inductor L has the helix shape, a radius of the inductor L may be constant or is not necessarily constant. Note that the inductor L may have a spiral shape or a helix shape that turns around the central axis Ax two or more turns.

The resonant circuit 20 has a predetermined resonant frequency $f0$. The resonant circuit 20 is, for example, an LC resonant circuit including a capacitor and the inductor L. The LC resonant circuit is an LC parallel resonant circuit in which the capacitor and the inductor L are connected in parallel, or an LC series resonant circuit in which the capacitor and the inductor L are connected in series. The resonant frequency $f0$ is determined by a capacitance value of the capacitor and an inductance value of the inductor L. When a high-frequency signal having a frequency equal to the resonant frequency $f0$ is input to the LC parallel resonant circuit, the impedance of the LC parallel resonant circuit is maximized. When the high-frequency signal having the frequency equal to the resonant frequency $f0$ is input to the LC series resonant circuit, the impedance of the LC series resonant circuit is minimized.

In an exemplary aspect, the resonant frequency $f0$ belongs to, for example, an ultrahigh frequency (UHF) frequency band. The UHF frequency band is a band to which a frequency of 300 MHz or more and 3 GHz or less belongs.

In one aspect, the wireless IC tag 14 is preferably attached to a general medical device belonging to Class I in the Japanese medical device nomenclature. Therefore, the metal medical instrument 12 is, for example, a general medical device belonging to Class I in the Japanese medical device nomenclature. In addition, it is recommended to attach the wireless IC tag 14 to a small steel article. Therefore, the metal medical instrument 12 is, for example, a small steel article. Examples of the small steel article include a gag, a retractor, forceps, an elevator, a peeler, a needle holder, a scalpel, scissors, a chisel, a curette, tweezers, a saw, a file, and a hook.

The metal medical instrument 12 includes a metal portion 16. The metal medical instrument 12 may include only the metal portion 16. In addition, the metal medical instrument 12 may include a configuration other than the metal portion 16. Therefore, the metal medical instrument 12 may include, for example, a resin portion, a rubber portion, and the like.

Preferably, the metal portion 16 is made of metal. Therefore, the metal portion 16 may be made of, for example, steel, iron, copper, or another metal or an alloy in various exemplary aspects.

When the wireless IC tag 14 is fixed to the metal portion 16 of the metal medical instrument 12, electric field coupling, magnetic field coupling, or electromagnetic field coupling is established between the resonant circuit 20 and the metal portion 16 of the metal medical instrument 12 so that the metal portion 16 of the metal medical instrument 12 performs either of functions (A) and/or (B) to be described later. For example, the wireless IC tag 14 may be fixed to the metal portion 16 of the metal medical instrument 12 with a resin adhesive. In addition, the wireless IC tag 14 may be fixed to the metal portion 16 of the metal medical instrument 12 by welding, for example.

In addition, the fact that the electric field coupling is established between the resonant circuit 20 and the metal portion 16 means, for example, that a transmission signal is supplied from the resonant circuit 20 to the metal portion 16 by an electric field and/or that a reception signal is supplied from the metal portion 16 to the resonant circuit 20 by an electric field. The fact that the magnetic field coupling is established between the resonant circuit 20 and the metal portion 16 means, for example, that a transmission signal is supplied from the resonant circuit 20 to the metal portion 16 by a magnetic field and/or that a reception signal is supplied from the metal portion 16 to the resonant circuit 20 by a magnetic field. The fact that the electromagnetic field coupling is established between the resonant circuit 20 and the metal portion 16 means, for example, that a transmission signal is supplied from the resonant circuit 20 to the metal portion 16 by an electromagnetic field and/or that a reception signal is supplied from the metal portion 16 to the resonant circuit 20 by an electromagnetic field.

The metal portion 16 of the metal medical instrument 12 emits the transmission signal, which has a frequency equal to the resonant frequency $f0$ and supplied from the resonant circuit 20, as an electromagnetic wave.

More specifically, the wireless IC chip 18 generates a transmission signal obtained by modulating a carrier wave having a frequency equal to the resonant frequency $f0$ with transmission data. The resonant circuit 20 resonates by the transmission signal supplied from the wireless IC chip 18. The resonant circuit 20 supplies the transmission signal having the frequency equal to the resonant frequency $f0$ to the metal portion 16. At this time, the strength of a signal having a frequency other than the resonant frequency $f0$, supplied from the resonant circuit 20 to the metal portion 16, is lower than the strength of the transmission signal having the frequency equal to the resonant frequency $f0$ supplied from the resonant circuit 20 to the metal portion 16. The metal portion 16 emits the transmission signal supplied from the resonant circuit 20 as the electromagnetic wave. That is, the metal portion 16 functions as an antenna that emits the electromagnetic wave. At this time, the metal portion 16 emits the electromagnetic wave from the entire metal portion 16. A reader/writer (not illustrated) can receive the electromagnetic wave, thereby receiving the transmission signal. In the present embodiment, it is noted that the transmission signal having the frequency equal to the resonant frequency f0 includes a case where the frequency of the transmission signal completely coincides with the resonant frequency f0 and a case where the frequency of the transmission signal is a frequency slightly deviated from the resonant frequency f0. For purposes of this disclosure, it is noted that the slight deviation from the resonant frequency f0 means, for example, a deviation of about several tens of MHz.

Moreover, the metal portion 16 of the metal medical instrument 12 can be configured to receive a reception signal having a frequency equal to the resonant frequency f0 as an electromagnetic wave, and to supply the reception signal to the resonant circuit 20.

More specifically, the reader/writer emits a reception signal, obtained by modulating a carrier wave having a frequency equal to the resonant frequency f0 with reception data, as an electromagnetic wave. The metal portion 16 receives the reception signal, obtained by modulating the carrier wave having the frequency equal to the resonant frequency f0 with reception data, as the electromagnetic wave. That is, the metal portion 16 is configured to function as an antenna that receives the electromagnetic wave. The metal portion 16 supplies the reception signal having the frequency equal to the resonant frequency f0 to the resonant circuit 20. At this time, the strength of a signal having a frequency other than the resonant frequency f0, supplied from the metal portion 16 to the resonant circuit 20, is lower than the strength of the reception signal having the frequency equal to the resonant frequency f0 supplied from the metal portion 16 to the resonant circuit 20. The resonant circuit 20 resonates by the reception signal supplied from the metal portion 16. The resonant circuit 20 supplies the reception signal having the frequency equal to the resonant frequency f0 to the wireless IC chip 18. The wireless IC chip 18 demodulates the reception signal to acquire the reception data. In the present specification, the reception signal having the frequency equal to the resonant frequency f0 includes a case where the frequency of the reception signal completely coincides with the resonant frequency f0 and a case where the frequency of the reception signal is a frequency slightly deviating from the resonant frequency f0. For purposes of this disclosure, it is reiterated that the slight deviation from the resonant frequency f0 can be, for example, a deviation of about several tens of MHz.

It is also noted that the wireless IC tag-attached metal medical instrument 10 receives, for example, the reception signal transmitted from the reader/writer, and reflects a part of the reception signal to transmit the transmission signal. Specifically, function (B) is performed by the metal portion 16 of the metal medical instrument 12 in the wireless IC tag-attached metal medical instrument 10. As a result, the wireless IC chip 18 demodulates the reception signal to acquire the reception data. In response, the wireless IC chip 18 generates a transmission signal obtained by modulating a carrier wave of the reception signal, received by the metal portion 16 of the metal medical instrument 12, with transmission data. The resonant circuit 20 resonates by the transmission signal supplied from the wireless IC chip 18. The resonant circuit 20 supplies the transmission signal having the frequency equal to the resonant frequency f0 to the metal portion 16. Thereafter, the metal portion 16 of the metal medical instrument 12 performs function (A).

Meanwhile, there is a case where a wireless IC tag-attached article and a reader/writer communicate with each other via a magnetic field. In such communication via the magnetic field, a high-frequency signal belonging to a HF frequency band is used. Therefore, a coil antenna is connected to a wireless IC tag. Then, magnetic field coupling is established between the reader/writer and the coil antenna so that the reader/writer and the wireless IC tag-attached article communicate with each other. On the other hand, the wireless IC tag-attached metal medical instrument 10 communicates with the reader/writer via the electromagnetic wave. That is, the wireless IC tag-attached metal medical instrument 10 communicates with the reader/writer via a high-frequency signal belonging to the UHF frequency band. Therefore, the metal portion 16 of the wireless IC tag-attached metal medical instrument 10 emits the electromagnetic wave instead of the magnetic field. According to the exemplary aspect, the metal portion 16 is not a coil antenna, and, therefore, does not have a coil shape. That is, the metal portion 16 does not have a spiral shape or a helix shape.

In addition, the metal portion 16 may have or does not necessarily have an electrical length equal to an integral multiple of a half wavelength of the resonant frequency f0. When the metal portion 16 has the electrical length equal to the integral multiple of the half wavelength of resonant frequency f0, the metal portion 16 functions as a dipole antenna. As a result, a standing wave is generated in the metal portion 16. For example, when the metal portion 16 has an electrical length equal to the half wavelength of the resonant frequency f0, the resonant frequency f0 coincides with a resonant frequency of the metal portion 16.

Meanwhile, the wireless IC tag-attached metal medical instrument 10 is excellent in that the high-frequency signal can be transmitted and/or received regardless of the electrical length of the metal portion 16. That is, the wireless IC tag-attached metal medical instrument 10 can be configured to transmit and/or receive the high frequency signal even when the electrical length of the metal portion 16 is not equal to the integral multiple of the half wavelength of the resonant frequency f0. In order for the wireless IC tag-attached metal medical instrument 10 to exhibit such an advantage, the frequency of the transmission signal and the frequency of the reception signal are equal to the resonant frequency f0 of the resonant circuit 20 in the wireless IC tag-attached metal medical instrument 10. Further, the resonant circuit 20 also functions as a matching circuit that achieves impedance matching between the wireless IC chip 18 and the metal portion 16. Thus, the impedance of the resonant circuit 20 is equal to the impedance of the wireless IC chip 18. Further, the electric field coupling, magnetic field coupling, or electromagnetic field coupling is established between the resonant circuit 20 and the metal portion 16. Thus, the resonant circuit 20 and the metal portion 16 are not electrically conducted. Accordingly, the relatively weak electric field coupling, magnetic field coupling, or electromagnetic field coupling is established between the resonant circuit 20 and the metal portion 16. As a result, the resonant frequency f0 of the resonant circuit 20 and the impedance of the resonant circuit 20 hardly vary even if the electrical length of the metal portion 16 varies. As a result, the resonant circuit 20 resonates by the high-frequency signal having the resonant frequency f0 regardless of the electrical length of the metal portion 16. Further, the impedance matching between the wireless IC chip 18 and the metal portion 16 is easily achieved regardless of the electrical length of the metal portion 16. Accordingly, the wireless IC tag-attached metal medical instrument 10 can transmit and/or receive the high-frequency signal having the frequency of the resonant frequency f0 regardless of the electrical length of the metal portion 16. It is noted that the wireless IC tag 14 can include the matching circuit separately from the resonant circuit 20 in an exemplary aspect. However, no matching circuit is provided outside the resonant circuit 20 in the exemplary embodiment.

As described above, the resonance at the resonant frequency f0 hardly occurs in the metal portion 16 when the electrical length of the metal portion 16 is not equal to the integral multiple of the half wavelength of the resonant frequency f0. That is, a standing wave having a length equal to the half wavelength of the resonant frequency f0 is hardly generated in the metal portion 16. In this case, the resonant frequency f0 is different from a frequency of the standing wave that can be generated in the metal portion 16. From the above viewpoint, the metal portion 16 does not necessarily have the electrical length equal to the integral multiple of the half wavelength of the resonant frequency f0.

It is noted that the wireless IC tag-attached metal medical instrument 10 can further include a resin portion that covers the wireless IC tag 14 such that the wireless IC tag 14 is not exposed. However, the wireless IC tag-attached metal medical instrument 10 does not necessarily include the resin portion in exemplary aspects.

Technical Effects

According to the wireless IC tag-attached metal medical instrument 10, the degree of freedom in a method for attaching the wireless IC tag 14 is improved. More specifically, in the wireless IC tag-attached metal medical instrument 10, the wireless IC tag 14 including the resonant circuit 20, which includes the inductor L having the spiral shape or helix shape that turns around the central axis Ax more than one turn, is fixed to the metal portion 16 of the metal medical instrument 12, so that the electric field coupling, magnetic field coupling, or electromagnetic field coupling is established between the resonant circuit 20 and the metal portion 16 of the metal medical instrument 12. That is, an inductance value of the inductor L is large in the wireless IC tag-attached metal medical instrument 10. As the inductance value of the inductor L increases, a Q-factor of the resonant circuit 20 decreases. Therefore, a communication band of the wireless IC tag-attached metal medical instrument 10 is widened. As a result, the wireless IC tag-attached metal medical instrument 10 can be configured to transmit and receive a high-frequency signal having a frequency slightly deviated from the resonant frequency f0 of the resonant circuit 20. Even when the resonant frequency f0 of the resonant circuit 20 of the wireless IC tag 14 varies due to a change in the method for attaching the wireless IC tag 14, the wireless IC tag-attached metal medical instrument 10 can transmit the high-frequency signal and/or receive the high frequency signal. As described above, the degree of freedom in the method for attaching the wireless IC tag 14 can be improved according to the wireless IC tag-attached metal medical instrument 10.

According to the wireless IC tag-attached metal medical instrument 10, the wireless IC tag 14 is configured to be fixed to the metal portion 16 of the metal medical instrument 12 with the resin adhesive, and thus, a fixing member or the like for fixing the wireless IC tag 14 to the metal portion 16 is unnecessary. Thus, it is easy to fix the wireless IC tag 14 to the metal portion 16.

According to the wireless IC tag-attached metal medical instrument 10, the wireless IC tag 14 may be fixed to the metal portion 16 of the metal medical instrument 12 by welding, and thus, detachment of the wireless IC tag 14 from the metal portion 16 due to an environmental change, such as a temperature change, is reduced.

In the wireless IC tag-attached metal medical instrument 10, the wireless IC tag 14 may be covered with the resin portion. Thus, the wireless IC tag 14 is protected by the resin portion.

In the wireless IC tag-attached metal medical instrument 10, the inductor L may have the spiral shape or helix shape that turns around the central axis Ax two or more turns. In this case, the inductance value of the inductor L becomes still larger. As a result, the Q-factor of the resonant circuit 20 decreases, and the communication band of the wireless IC tag-attached metal medical instrument 10 becomes wider.

First Example

[Configuration of Wireless IC Tag-Attached Metal Medical Instrument]

Figure 2:
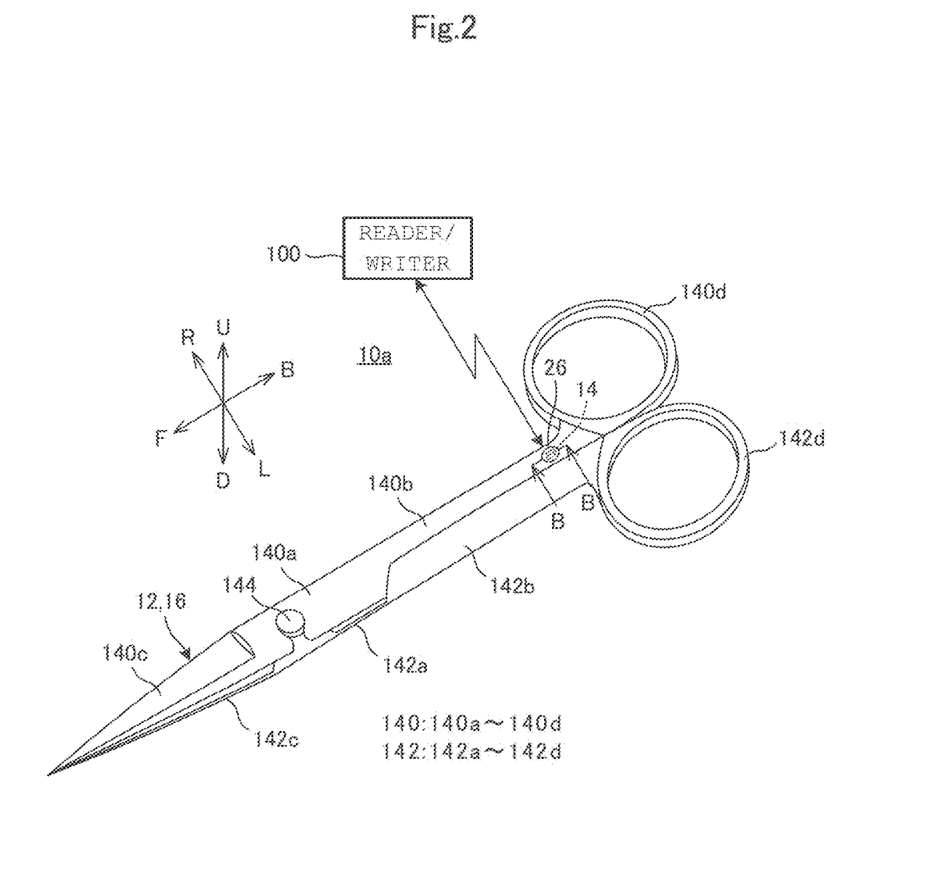
FIG. 2 is an external perspective view of a wireless IC tag-attached metal medical instrument 10a according to a first example.
Figure 3:
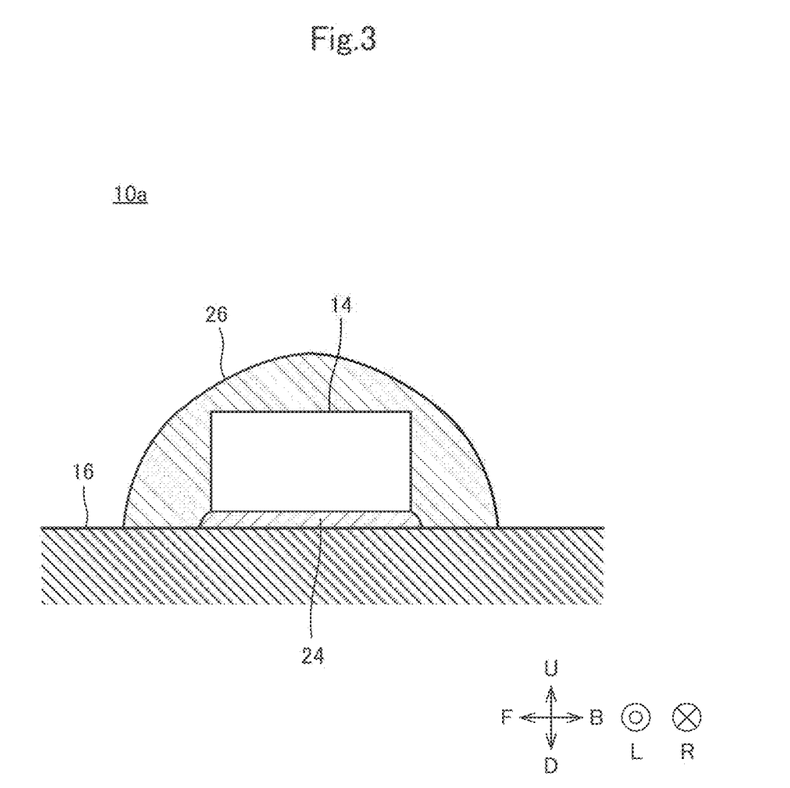
FIG. 3 is a cross-sectional view taken along line B-B in FIG. 2.
Figure 4:
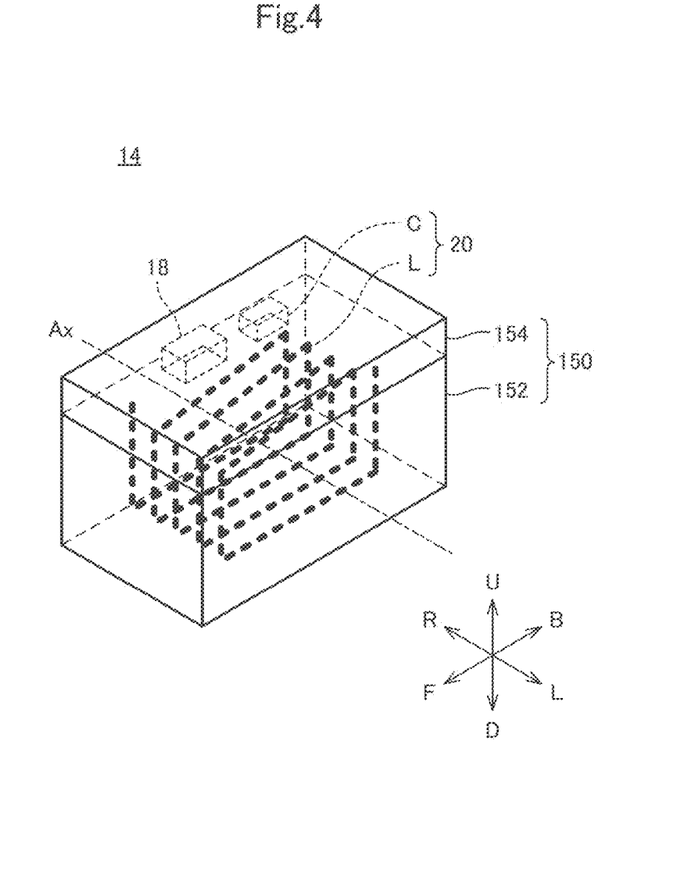
FIG. 4 is a perspective view of a wireless IC tag 14.
Figure 5:
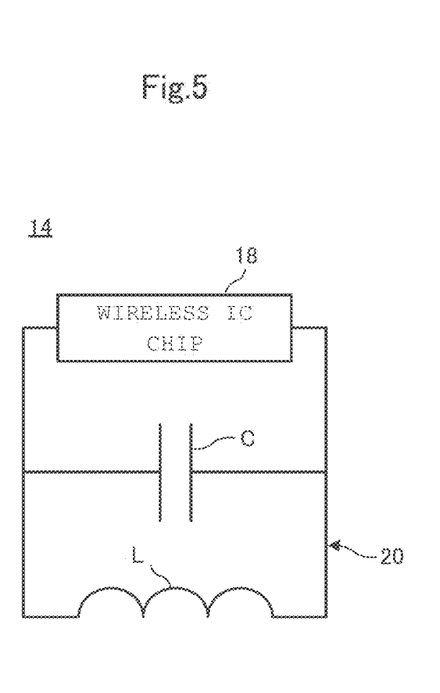
FIG. 5 is an equivalent circuit diagram of the wireless IC tag 14.

Next, a wireless IC tag-attached metal medical instrument 10a according to a first example will be described with reference to the drawings. FIG. 2 is an external perspective view of the wireless IC tag-attached metal medical instrument 10a according to the first example. FIG. 3 is a cross-sectional view taken along line B-B in FIG. 2. FIG. 4 is a perspective view of the wireless IC tag 14. FIG. 5 is an equivalent circuit diagram of the wireless IC tag 14.

Hereinafter, a front-back direction of the wireless IC tag-attached metal medical instrument 10a is referred to as the front-back direction. The front-back direction is a direction in which blades of scissors as the wireless IC tag-attached metal medical instrument 10a extend. An up-down direction of the wireless IC tag-attached metal medical instrument 10a is referred to as the up-down direction. The up-down direction is a direction in which the two blades of the scissors as the wireless IC tag-attached metal medical instrument 10a overlap each other. A left-right direction of the wireless IC tag-attached metal medical instrument 10a is referred to as the left-right direction. A forward direction of the wireless IC tag-attached metal medical instrument 10a is referred to as the forward direction. A backward direction of the wireless IC tag-attached metal medical instrument 10a is referred to as the backward direction. A left direction of the wireless IC tag-attached metal medical instrument 10a is referred to as the left direction. A right direction of the wireless IC tag-attached metal medical instrument 10a is referred to as the right direction. An upward direction of the wireless IC tag-attached metal medical instrument 10a is referred to as the upward direction. A downward direction in the wireless IC tag-attached metal medical instrument 10a is referred to as the downward direction.

As illustrated in FIG. 2, the wireless IC tag-attached metal medical instrument 10a includes the metal medical instrument 12 and the wireless IC tag 14.

The metal medical instrument 12 is scissors in this example. The metal medical instrument 12 includes a metal portion 16. In the present embodiment, the metal medical instrument 12 includes only the metal portion 16. Thus, the metal medical instrument 12 does not include a resin portion or a rubber portion.

The metal portion 16 includes a first shaving member 140, a second shaving member 142, and a screw 144. The first shaving member 140 includes a first support portion 140a (also referred to as a "first support"), a first body portion 140b (also referred to as a "first body"), a first blade portion 140c (also referred to as a "first blade"), and a first ring portion 140d (also referred to as a "first ring" or a "first gripping member"). The second shaving member 142 includes a second support portion 142a (also referred to as a "second support"), a second body portion 142b (also referred to as a "second body"), a second blade portion 142c (also referred to as a "second blade"), and a second ring portion 142d (also referred to as a "second ring" or a "second gripping member").

As shown, the first support portion 140a has a flat plate shape extending in the front-back direction. The second support portion 142a has a flat plate shape extending in the front-back direction. The first support portion 140a is disposed on the second support portion 142a.

The first blade portion 140c has a flat plate shape extending in the forward direction from a front end of the first support portion 140a. A blade is provided on a right edge of the first blade portion 140c. The second blade portion 142c has a flat plate shape extending in the forward direction from a front end of the second support portion 142a. A blade is provided on a left edge of the second blade portion 142c. The first blade portion 140c is disposed on the second blade portion 142c.

Moreover, the first body portion 140b has a rod shape extending in a backward direction B from a back end of the first support portion 140a. Likewise, the second body portion 142b has a rod shape extending in the backward direction B from a back end of the second support portion 142a. The first body portion 140b is disposed on the right of the second body portion 142b.

The first ring portion 140d is connected to the back end of the first body portion 140b. The first ring portion 140d has an annular shape when viewed in the downward direction. The second ring portion 142d is connected to a back end of the second body portion 142b. The second ring portion 142d has an annular shape when viewed in the downward direction. The first ring portion 140d is disposed on the right of the second ring portion 142d.

The screw 144 (generally referred to as a "coupling member") penetrates through the first support portion 140a and the second support portion 142a in the up-down direction. As a result, the second shaving member 142 can rotate about a central axis of the screw 144 relative to the first shaving member 140.

In an exemplary aspect, the metal medical instrument 12 as described above is the scissors, which is a general medical device belonging to Class I in the Japanese Medical Device Nomenclature. In addition, the metal medical instrument 12 is the scissors, and thus, is a small steel article.

As further shown, the wireless IC tag 14 has a rectangular parallelepiped shape. The wireless IC tag 14 is fixed to a back portion of an upper surface of the first body portion 140b. The wireless IC tag 14 is fixed to the metal portion 16 with a resin adhesive 24 as illustrated in FIG. 3. Specifically, the resin adhesive 24 is in contact with both a bottom surface of the wireless IC tag 14 and the metal portion 16. The resin adhesive 24 is applied to the entire bottom surface of the wireless IC tag 14. The resin adhesive 24 is made of, for example, an epoxy resin.

The wireless IC tag-attached metal medical instrument 10a further includes a resin portion 26. As illustrated in FIG. 3, the resin portion 26 covers the wireless IC tag 14. As a result, the wireless IC tag 14 is not exposed. The resin portion 26 is made of, for example, an epoxy resin.

As illustrated in FIG. 4, the wireless IC tag 14 further includes the wireless IC chip 18, the resonant circuit 20, and a body 150. The body 150 has a rectangular parallelepiped shape. The body 150 includes a body lower portion 152 and a body upper portion 154. The body lower portion 152 is, for example, a laminate. The body lower portion 152 has a rectangular parallelepiped shape. The laminate has a structure in which a plurality of insulator layers having main surfaces perpendicular to the left-right direction are laminated in the left-right direction. However, a lamination direction of the laminate may be the up-down direction or the front-back direction. The laminate is made of, for example, a glass epoxy resin. The body upper portion 154 is, for example, a resin member. The body upper portion 154 has, for example, a rectangular parallelepiped shape. The resin member is made of, for example, an epoxy resin.

The wireless IC chip 18 is a semiconductor integrated circuit. The wireless IC chip 18 is mounted on an upper surface of the body lower portion 152. The wireless IC chip 18 includes a memory that stores predetermined information. In addition, the wireless IC chip 18 includes a modulator that modulates a carrier wave with transmission data stored in the memory to generate a transmission signal. In addition, the wireless IC chip 18 includes a demodulator that demodulates reception data from a reception signal obtained by modulating a carrier wave with the reception data.

The resonant circuit 20 includes a capacitor C and an inductor L. In the exemplary aspect, the capacitor C is a chip capacitor. As further shown, the capacitor C is mounted on the upper surface of the body lower portion 152. The inductor L is provided in the body lower portion 152. The inductor L has a spiral shape. The inductor L has a helix shape that turns two or more turns around the central axis Ax extending in the left-right direction. The inductor L includes a plurality of conductor layers and a plurality of via-hole conductors. Specifically, each of the plurality of conductor layers is formed on main surfaces of the plurality of insulator layers. Each of the plurality of conductor layers turns about the central axis Ax when viewed in the right direction. Each of the plurality of via-hole conductors penetrates through the plurality of insulator layers in the left-right direction. Each of the plurality of via-hole conductors connects ends of conductor layers adjacent to each other in the left-right direction.

As illustrated in FIG. 5, the capacitor C and the inductor L are connected in parallel to the wireless IC chip 18 by a wiring (not illustrated in FIG. 4). Thus, the resonant circuit 20 is an LC parallel resonator.

It is noted that the attachment position of the wireless IC tag 14 with respect to the metal portion 16 is not limited to the position illustrated in FIG. 2. The wireless IC tag 14 may be attached to any of the first support portion 140a, the first body portion 140b, the first blade portion 140c, the first ring portion 140d, the second support portion 142a, the second body portion 142b, the second blade portion 142c, and the second ring portion 142d.

Next, an operation when the wireless IC tag-attached metal medical instrument 10a transmits a transmission signal will be described. Meanwhile, the operation of the wireless IC tag-attached metal medical instrument 10a is the same as the operation of the wireless IC tag-attached metal medical instrument 10. Therefore, the description will be given focusing on operations of the metal portion 16 and the resonant circuit 20.

The resonant circuit 20 resonates by the transmission signal generated by the wireless IC chip 18. As a result, the inductor L generates a magnetic flux extending in the left-right direction. This magnetic flux turns around the metal portion 16 when viewed in the backward direction.

Therefore, magnetic field coupling is established between the resonant circuit 20 and the metal portion 16. As a result, a current flows through the metal portion 16 in the front-back direction. However, a direction of the magnetic flux varies at the resonant frequency f0, a direction of the current also varies at the resonant frequency f0. As a result, an electromagnetic wave is emitted from the entire metal portion 16 by electromagnetic induction.

Next, an operation when the wireless IC tag-attached metal medical instrument 10a receives a reception signal will be described. Meanwhile, the operation of the wireless IC tag-attached metal medical instrument 10a is the same as the operation of the wireless IC tag-attached metal medical instrument 10. Therefore, the description will be given focusing on operations of the metal portion 16 and the resonant circuit 20.

The metal portion 16 receives a magnetic field, and a direction of the magnetic field varies at the resonant frequency f0. As a result, a current flows through the metal portion 16 in the front-back direction. However, a direction of the current flowing through the metal portion 16 also varies at the resonant frequency f0 since the direction of the magnetic field received by the metal portion 16 varies at the resonant frequency f0. As a result, the magnetic field turning around the metal portion 16 is generated by electromagnetic induction when viewed in the backward direction. This magnetic field passes through the inductor L in the left-right direction. In addition, a direction of the magnetic field passing through the inductor L varies at the resonant frequency f0. As a result, the resonant circuit 20 resonates by the magnetic field passing through the inductor L in the left-right direction, and supplies the reception signal having the frequency equal to the resonant frequency f0 to the wireless IC tag 14.

Technical Effects

According to the wireless IC tag-attached metal medical instrument 10a, the degree of freedom in a method for attaching the wireless IC tag 14 can be improved for the same reason as that in the wireless IC tag-attached metal medical instrument 10. In addition, according to the wireless IC tag-attached metal medical instrument 10a, it is easy to fix the wireless IC tag 14 to the metal portion 16 for the same reason as that in the wireless IC tag-attached metal medical instrument 10. According to the wireless IC tag-attached metal medical instrument 10a, the wireless IC tag 14 is protected by the resin portion 26 for the same reason as that in the wireless IC tag-attached metal medical instrument 10. According to the wireless IC tag-attached metal medical instrument 10a, a communication band of the wireless IC tag-attached metal medical instrument 10a becomes wider for the same reason as that in the wireless IC tag-attached metal medical instrument 10.

Second Example

Figure 6:
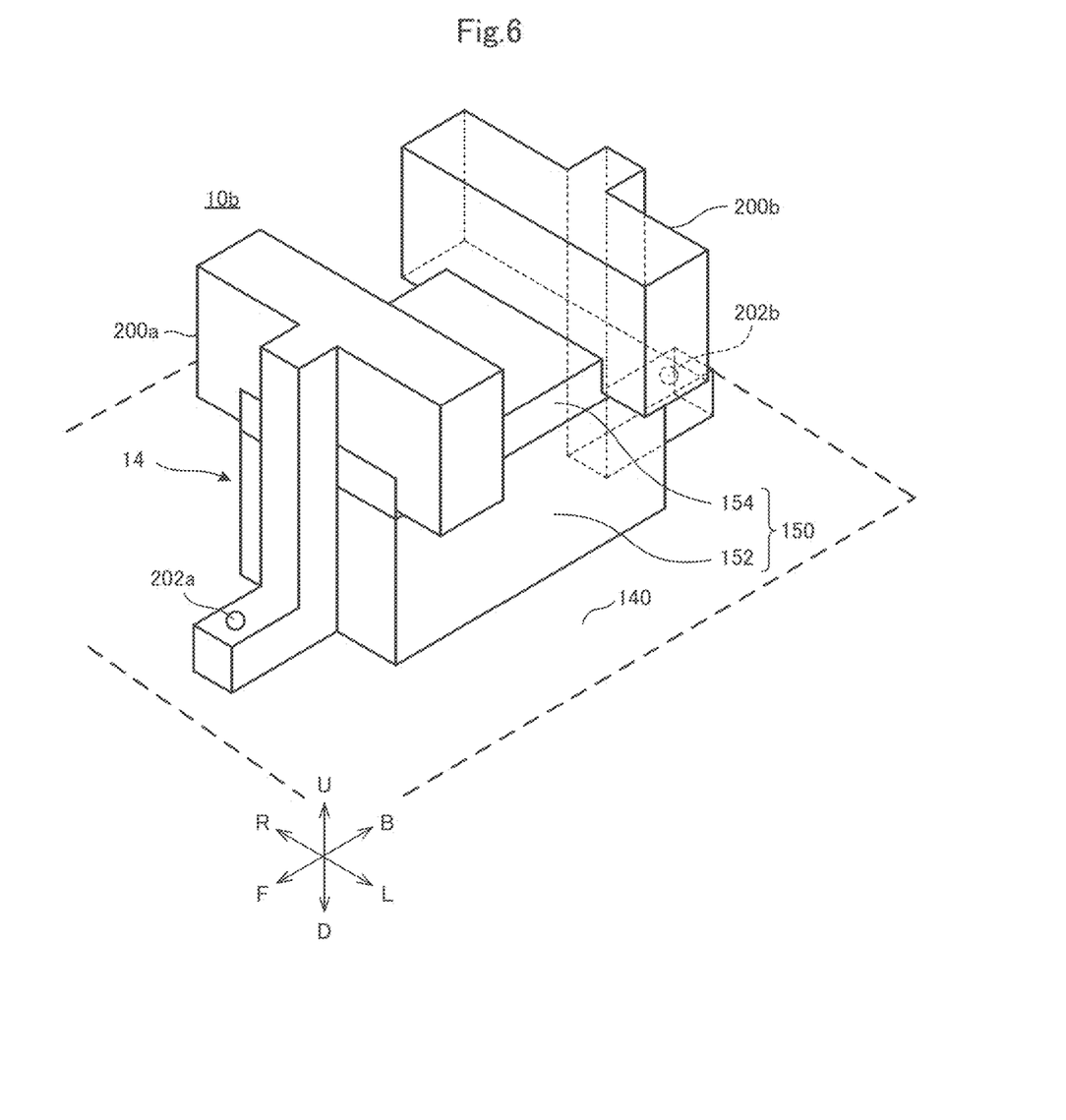
FIG. 6 is an external perspective view of the wireless IC tag 14 of a wireless IC tag-attached metal medical instrument 10b according to a second example.

Next, a wireless IC tag-attached metal medical instrument 10b according to a second example will be described with reference to the drawings. FIG. 6 is an external perspective view of the wireless IC tag 14 of the wireless IC tag-attached metal medical instrument 10b according to a second modification of the exemplary embodiment.

As shown, the wireless IC tag-attached metal medical instrument 10b is different from the wireless IC tag-attached metal medical instrument 10a in terms of a method for fixing the wireless IC tag 14. More specifically, the wireless IC tag 14 is fixed to the metal portion 16 by welding in the wireless IC tag-attached metal medical instrument 10b. The wireless IC tag 14 is fixed to the first shaving member 140 or the second shaving member 142 by welding. The wireless IC tag-attached metal medical instrument 10b includes fixing members 200a and 200b. Then, the wireless IC tag 14 is fixed to the first shaving member 140 or the second shaving member 142 via the fixing members 200a and 200b welded to the first shaving member 140 or the second shaving member 142. In the present embodiment, the wireless IC tag 14 is fixed to the first shaving member 140 via the fixing members 200a and 200b welded to the first shaving member 140.

The fixing members 200a and 200b are metal members. The fixing member 200a is in contact with an upper surface and a front surface of the body 150 of the wireless IC tag 14. Then, a front end portion of the fixing member 200a is fixed to the first shaving member 140 via a welded portion 202a. Accordingly, the welded portion 202a where the fixing member 200a is welded to the first shaving member 140 is positioned in front of the wireless IC tag 14.

The fixing member 200b has the same structure as the fixing member 200a. Specifically, the fixing member 200b is in contact with the upper surface and a back surface of the body 150 of the wireless IC tag 14. Then, a back end portion of the fixing member 200b is fixed to the first shaving member 140 via a welded portion 202b. Therefore, the welded portion 202b where the fixing member 200b is welded to the first shaving member 140 is positioned at the back of the wireless IC tag 14.

It is noted that the wireless IC tag 14 may be covered with a resin portion (not illustrated in FIG. 6) in an alternative aspect.

It is also noted that the wireless IC tag 14 may be fixed to the second shaving member 142 via the fixing members 200a and 200b. In this case, the welded portion 202a where the fixing member 200a is welded to the second shaving member 142 is positioned in front of the wireless IC tag 14. The welded portion 202b where the fixing member 200b is welded to the second shaving member 142 is positioned at the back of the wireless IC tag 14.

According to the wireless IC tag-attached metal medical instrument 10b, the degree of freedom in a method for attaching the wireless IC tag 14 is improved for the same reason as that in the wireless IC tag-attached metal medical instruments 10 and 10a. According to the wireless IC tag-attached metal medical instrument 10b, detachment of the wireless IC tag 14 from the metal portion 16 due to an environmental change, such as a temperature change, is reduced for the same reason as that of the wireless IC tag-attached metal medical instrument 10. According to the wireless IC tag-attached metal medical instrument 10b, the wireless IC tag 14 is protected by the resin portion for the same reason as that in the wireless IC tag-attached metal medical instruments 10 and 10a.

Additional Embodiments

The embodiment and examples for which at least one of the description and illustration has been given in the present specification are intended to facilitate the understanding of the present disclosure, and do not limit an idea of the present disclosure. The above embodiment and examples can be changed and improved without departing from a spirit thereof.

It is noted that the spirit includes equivalent elements, modifications, deletions, combinations (for example, combinations of features across the embodiment and examples), improvements, and changes that can be recognized by those skilled in the art based on the embodiment and examples disclosed herein.

Such embodiment and examples should be construed to be non-exclusive. For example, in the present specification, the terms "preferably" and "preferable" are non-exclusive terms, and mean that "it is preferred but does not impose any limitation thereon" and "it is preferable but does not impose any limitation thereon".

REFERENCE SIGNS LIST 10, 10a, 10b wireless IC tag-attached metal medical instrument
12 metal medical instrument
14 wireless IC tag
16 metal portion
18 wireless IC chip
20 resonant circuit
24 resin adhesive
26 resin portion
140 first shaving member
140a first support portion
140b first body portion
140c first blade portion
140d first ring portion
142 second shaving member
142a second support portion
142b second body portion
142c second blade portion
142d second ring portion
144 screw
150 body
152 body lower portion
154 body upper portion
200a, 200b fixing member
202a, 202b welded portion
Ax central axis
C capacitor
L inductor

The invention claimed is:

1. A wireless IC tag-attached metal medical instrument comprising:
a wireless IC tag that includes a resonant circuit having an inductor, and a wireless IC chip, with the resonant circuit being electrically connected to the wireless IC chip and having a predetermined resonant frequency, and the inductor having a spiral shape or a helix shape that turns around a central axis more than one turn; and
a metal medical instrument that includes a metal portion and that is configured such that electric field coupling, magnetic field coupling, or electromagnetic field coupling is established between the resonant circuit and the metal portion of the metal medical instrument, and the metal portion is configured to emit a transmission signal or receive a reception signal when the wireless IC tag including the resonant circuit is fixed to the metal portion of the metal medical instrument,
wherein, when the metal portion emits the transmission signal, the metal portion is configured to emit the transmission signal at a frequency equal to the predetermined resonant frequency and that is supplied from the resonant circuit as an electromagnetic wave, and
wherein, when the metal portion receives the reception signal, the metal portion is configured to receive the reception signal at a frequency equal to the predetermined resonant frequency, and to supply the reception signal to the resonant circuit.

2. The wireless IC tag-attached metal medical instrument according to claim 1, wherein the metal medical instrument is a medical device belonging to Class I in Japanese Medical Device Nomenclature.

3. The wireless IC tag-attached metal medical instrument according to claim 1, wherein the metal medical instrument is a steel article.

4. The wireless IC tag-attached metal medical instrument according to claim 1, further comprising a resin portion that covers the wireless IC tag such that the wireless IC tag is not externally exposed.

5. The wireless IC tag-attached metal medical instrument according to claim 1, wherein the inductor has a spiral shape or a helix shape that turns around the central axis two or more turns.

6. The wireless IC tag-attached metal medical instrument according to claim 1, further comprising a resin adhesive that fixes the wireless IC tag to the metal portion of the metal medical instrument.

7. The wireless IC tag-attached metal medical instrument according to claim 1, wherein the wireless IC tag is fixed to the metal portion of the metal medical instrument by a welding.

8. The wireless IC tag-attached metal medical instrument according to claim 1, wherein the predetermined resonant frequency is in an ultrahigh frequency (UHF) frequency band.

9. The wireless IC tag-attached metal medical instrument according to claim 1, wherein the wireless IC tag-attached metal medical instrument is configured to communicate with a reader/writer via an electromagnetic wave.

10. The wireless IC tag-attached metal medical instrument according to claim 1, wherein the wireless IC tag further includes a body having rectangular parallelepiped shape and that comprises a body lower portion formed of a plurality of insulator layers and a body upper portion disposed on the body lower portion.

11. The wireless IC tag-attached metal medical instrument according to claim 10, wherein the resonant circuit further includes a chip capacitor disposed on an upper surface of the body lower portion, and wherein the inductor is disposed in the body lower portion.

12. A wireless IC tag-attached metal medical instrument comprising:
a wireless IC tag that includes a wireless IC chip and a resonant circuit electrically connected to the wireless IC chip and having a predetermined resonant frequency, and an inductor having a spiral shape or a helix shape that turns around a central axis more than one turn; and
a metal medical instrument that includes a metal portion and that is configured such that electric field coupling, magnetic field coupling, or electromagnetic field coupling is established between the resonant circuit and the metal portion of the metal medical instrument, and the metal portion is configured to emit a transmission signal or receive a reception signal when the wireless IC tag including the resonant circuit is fixed to the metal portion of the metal medical instrument.

13. The wireless IC tag-attached metal medical instrument according to claim 12, wherein the metal portion of the metal medical instrument is configured to emit the transmission signal having a frequency equal to the predetermined resonant frequency and that is supplied from the resonant circuit as an electromagnetic wave.

14. The wireless IC tag-attached metal medical instrument according to claim 12, wherein the metal portion of the metal medical instrument is configured to receive the reception signal having a frequency equal to the predetermined resonant frequency as an electromagnetic wave, and to supply the reception signal to the resonant circuit.

15. The wireless IC tag-attached metal medical instrument according to claim 12, wherein the metal medical instrument is a steel article.

16. The wireless IC tag-attached metal medical instrument according to claim 12, further comprising a resin portion that covers the wireless IC tag such that the wireless IC tag is not externally exposed.

17. The wireless IC tag-attached metal medical instrument according to claim 12, wherein the inductor has a spiral shape or a helix shape that turns around the central axis two or more turns.

18. The wireless IC tag-attached metal medical instrument according to claim 12, further comprising a resin adhesive that fixes the wireless IC tag to the metal portion of the metal medical instrument.

19. The wireless IC tag-attached metal medical instrument according to claim 12, wherein the wireless IC tag is fixed to the metal portion of the metal medical instrument by a welding.

20. The wireless IC tag-attached metal medical instrument according to claim 12, wherein the predetermined resonant frequency is in an ultrahigh frequency (UHF) frequency band.

\* \* \* \* \*